United States Patent [19]

Coleman et al.

[11] Patent Number: 4,686,713
[45] Date of Patent: Aug. 18, 1987

[54] VISOR AND ASSEMBLY METHOD FOR VISOR

[75] Inventors: Ann C. Coleman; Irene E. Garza, both of San Antonio, Tex.

[73] Assignee: Texace Corporation, San Antonio, Tex.

[21] Appl. No.: 935,124

[22] Filed: Nov. 26, 1986

Related U.S. Application Data

[63] Continuation of Ser. No. 692,824, Jan. 18, 1985, abandoned.

[51] Int. Cl.⁴ ............................................... A61F 9/04
[52] U.S. Cl. ............................................ 2/12; 2/195
[58] Field of Search ...................... 2/12, 195, 197, 200, 2/171, 171.1, 192

[56] References Cited

U.S. PATENT DOCUMENTS

| | | |
|---|---|---|
| 217,500 | 7/1879 | White .......................................... 2/12 |
| 1,563,611 | 12/1925 | Cohen .......................................... 2/12 |
| 1,590,409 | 6/1926 | Bender ..................................... 2/12 X |
| 2,579,196 | 12/1951 | Lev ............................................ 2/195 |
| 3,133,289 | 5/1964 | Lipschultz ................................. 2/195 |
| 4,023,212 | 5/1977 | Huffman ................................ 2/171.1 |
| 4,293,958 | 10/1981 | Zauner ........................................ 2/12 |
| 4,606,077 | 8/1986 | Phillips ....................................... 2/12 |
| 4,621,378 | 11/1986 | Hatchman ............................. 2/12 X |

Primary Examiner—Peter Nerbun
Attorney, Agent, or Firm—Cox & Smith Inc.

[57] ABSTRACT

A high-quality, cloth visor which does not completely encircle the head and a method for assembling the same. All seams are hidden with no exposed edges of cloth on the exterior of the visor that can be snagged or unraveled.

12 Claims, 13 Drawing Figures

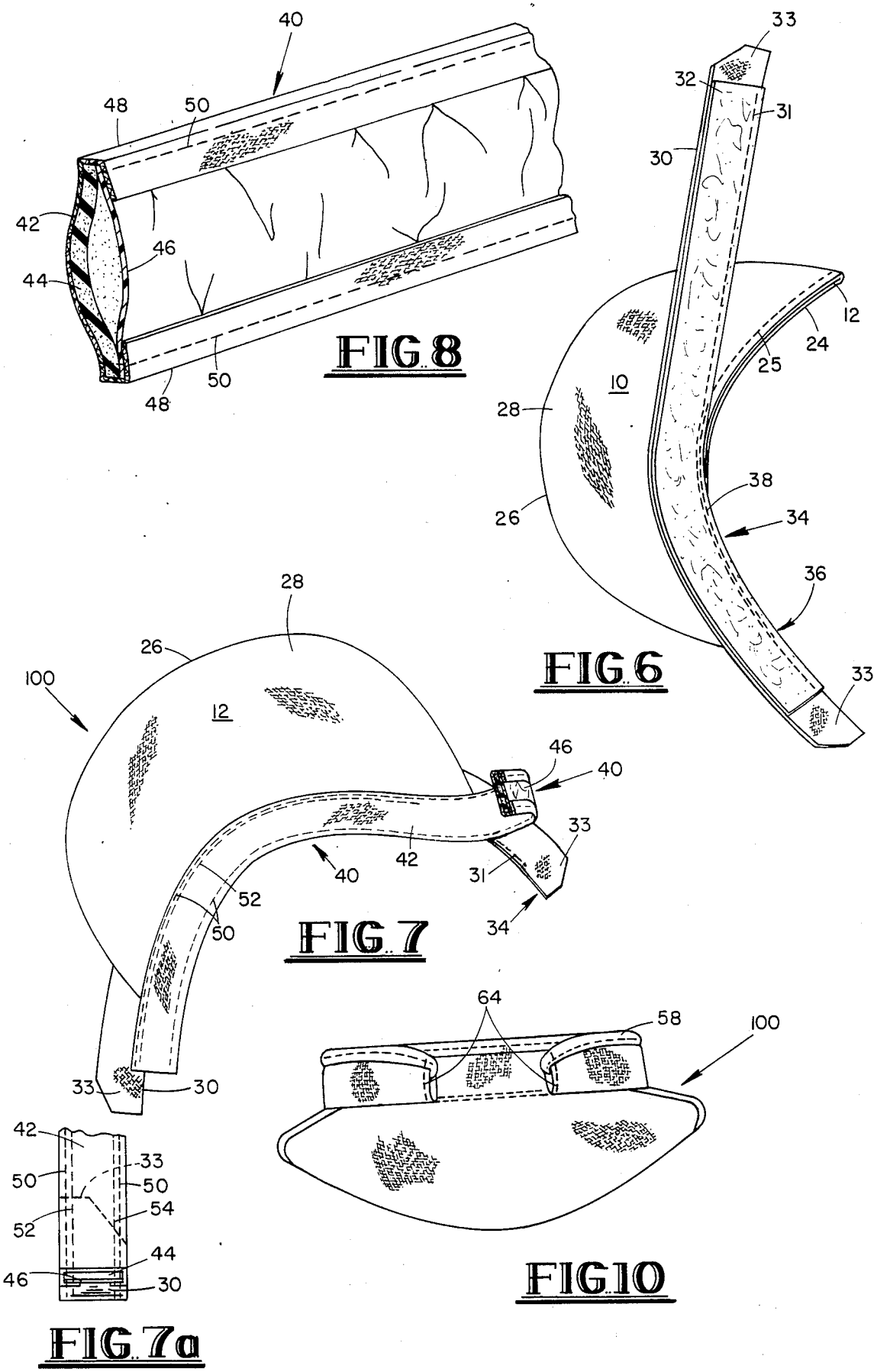

U.S. Patent  Aug. 18, 1987  Sheet 3 of 3  4,686,713
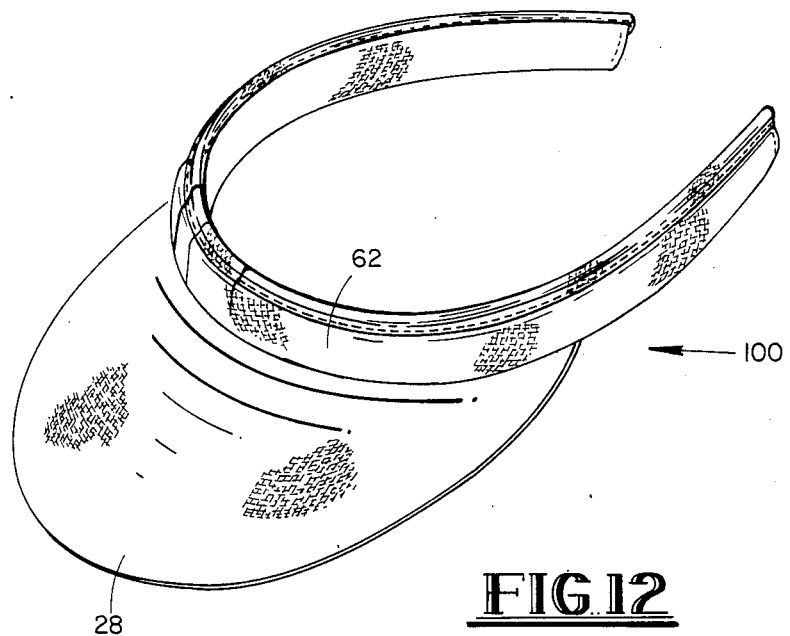
FIG.12
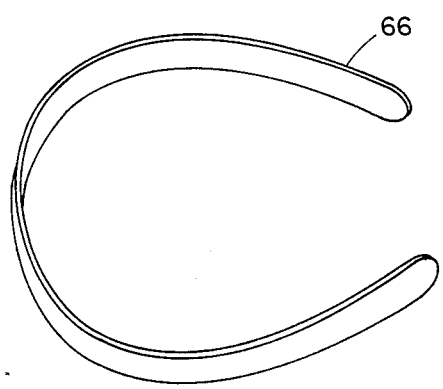
FIG.11
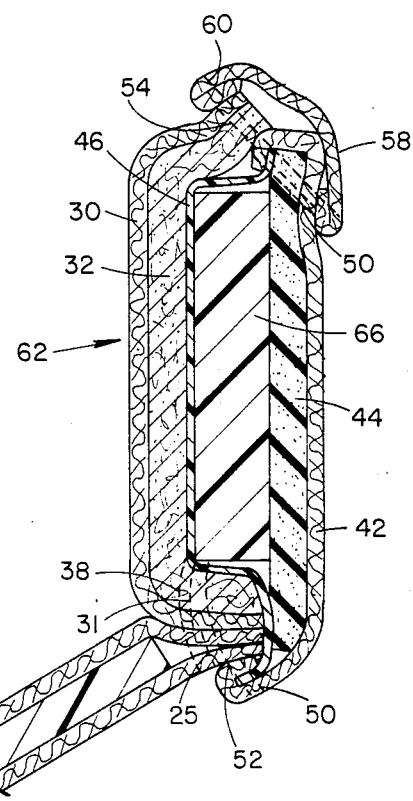
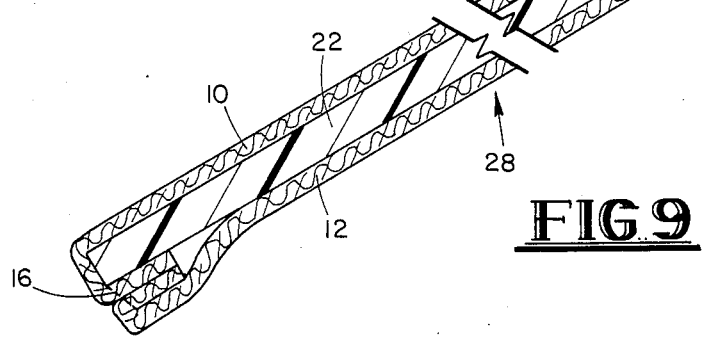
FIG.9

VISOR AND ASSEMBLY METHOD FOR VISOR

This application is a continuation of co-pending application Ser. No. 692,824, filed Jan. 18, 1985, now abandoned.

BACKGROUND OF THE INVENTION

The present invention relates to a method of assembling a visor. More particularly, the present invention relates to a method for assembling a high-quality, cloth covered visor with a partial headband which does not completely encircle the head.

Among the wide variety of products manufactured by hatters and millineries is a variety of a cap known as a visor. A visor can broadly be described as an open-headed cap with a bill. Visors have long been desirable for certain wearers because the lack of covering along the top of the head makes them lighter, cooler, and more comfortable than most caps.

Among visors, several varieties are known to exist in the art. Most of those which exist employ a feature found in most hats: a hatband. The hatband completely encircles the head and holds the visor in place by pressure at all points along the circumference of the head of a person. However, this feature is found to be too restrictive and uncomfortable for some hat wearers. In particular, a hatband which completely encircles the head is disfavored because it must be worn on top of the hair of a person. For persons with longer hair, especially women, this has the deleterious effect of causing the hair to mat down and leave a ring around the persons head when the visor is removed.

In order to simultaneously obtain all the advantages of an open, comfortable, light-weight visor which does not mess up a person's hair, it has been known in the art by some manufacturers of which the Applicant is aware to produce a visor which uses a partial hatband or headband instead of one completely encircling the head. However, all manufacturers of this variation of visor of which the Applicant is aware manufacture a plastic one-piece visor, which is considered of lesser quality and more uncomfortable than cloth hats. The partial headband can be made in several ways. First, it can be manufactured in a configuration similar to that of an ear piece of a pair of glasses i.e., holding the visor in place by resting on top of the ears. A second, and preferred variation, provides for a semi-rigid, semi-circular headband. The side members of the partial headband are made of a sufficiently rigid material so that they engage the front, sides and portions of the back part of the head to hold the visor in place. For persons with longer hair, the ear piece design and the semi-circular design can be placed underneath the hair so as not to mat it down. As stated, as far as is known, all currently available visors using the partial headbands are molded as a single piece of plastic. However, plastic is undesirable because it is a less comfortable material to be worn next to the skin. It has long been known that cloth or leather are more desirable substances from which to manufacture headwear because of their softer and more porous nature. However, cloth or leather visors cannot be molded from a single piece and still adequately grip the head or maintain the desired shape.

Applicant is not aware of any known method for manufacturing a durable, high-quality cloth visor with a partial headband. The present method for quickly and efficiently assembling such visors is very different from the assembly method for caps and other forms of headwear, because a cap or hat which completely covers the head is essentially a continuous piece of material joined together in a manner which gives the material a shape for fitting a person's head. For example, a hat made of straw or an animal pelt starts as a solid piece of material. The material is then stretched and formed by heat or other methods to form a bulge or "crown" in the center of the material. The crown envelopes the wearer's head, and the remainder of the material forms the brim. The circumference of the crown will be kept constant by attaching a hatband to the interior or exterior of the crown. For most caps, the crown will be formed from a separate piece of material and will be fixed by a headband. The cap crown will then be attached to a separate piece of material which has already been shaped to form a bill or brim.

Thus, the manufacturer of most hats and caps requires only one or two major steps to assemble the major structural part of the headwear. More importantly, the assembly can be completed fairly easily with all seams on the inside of the cap or hat. It is a practical necessity that any seams be hidden from the exterior for two reasons. First, the seams are unsightly and difficult to incorporate into the exterior design of the hat or cap. Second, exterior seams are more exposed to elements which could snag, tear or unravel the seams. It is relatively simple to assemble a cap with all seams facing the inside of the cap, and in fact, the crown, headband, and bill can be joined together in one step by sewing the headband on top of the bill and to the crown. This method results in all seams being hidden underneath the headband.

For a visor which completely encircles the head, the assembly method is equally as simple as for most hats and caps. One may essentially dispense with the piece of material forming the crown because there is no crown on a visor. Thus, the headband can be attached directly to the bill of the visor and the major structural elements of the visor are assembled with the seam being hidden underneath the headband.

For a visor which does not completely encircle the head, particular difficulties in assembly arise when it is desired to obtain a visor with hidden seams. To manufacture a cloth covered visor of this type, it is necessary to cover a fairly rigid material with cloth and attach a bill in order to assemble the major elements. The fairly rigid material is used to form the backbone of the partial headband, but it must be softened by a cloth covering in order to maintain comfort. On the other hand, full headbands do not necessarily require a softening agent as a covering, because these bands can rely on their ability to completely encircle and grip the head as sufficient support for the bill or brim. In other words, a full headband can be made solely of cloth or any other comfortable material, but will still be adequate support for the visor bill if the circumference of the cloth headband is small enough. But a partial headband made solely of cloth would not perform adequately and does not have enought rigidity to press against the sides of the head with adequate force to prevent the weight of the visor bill from causing the partial headband to slip. This necessitates the use of a semi-rigid material as a backbone for the partial headband. As mentioned, the material used for partial headbands by some manufacturers is plastic when the visors are molded of a single piece of plastic. However, plastic is uncomfortable next to the skin and is unattractive to users desiring a high-quality visor. Therefore, the problem faced and solved by the present invention is providing a method for covering a semi-rigid material in a partial headband with cloth and attaching the completed partial headband to a visor bill, but ensuring that these major structural elements form a comfortable, durable and attractive visor with no exposed seams.

In order to overcome the disadvantages mentioned above, the Applicant has invented a new and useful visor, and method for assembling the same, which produces a high-quality, durable and attractive cloth visor which does not have a headband which completely encircles the head. Therefore, it is an object of this invention to produce durable, high-quality cloth visors which are comfortable to the wearer. Furthermore, it is an object of the present invention to produce visors which do not cause the hair to mat down. Furthermore, it is an object of the present invention to produce visors which may be assembled rapidly. Furthermore, it is an object of the present invention to produce a visor which has the majority of its seams tucked or hidden from the exterior of the visor. Other objects of the invention will become evident as the invention is explained.

SUMMARY OF THE INVENTION

A visor and method for assembling the same which is substantially cloth covered and does not completely encircle the head of a person, comprising the steps of the forming of a bill, fixably mounting a headpiece means to said bill, and securing a headband forming means to said head piece means such that the head piece means is relatively firmly held against the head of a person. If constructed of cloth or leather, the method will result in a visor which has no seams formed on the exterior of the visor. The headband forming means will be enveloped inside the head piece means unless the headband forming means and head piece means are integral. The visor is assembled by sewing if the material used so permits.

DESCRIPTION OF THE DRAWINGS

FIG. 6 is a top view of the visor during the assembly of the sweat band to the visor.

FIGS. 7 and 7A are bottom views of the visor during the assembly of the sweat band to the visor.

FIG. 8 is a side perspective and cross-sectional view of the sweat band.

FIG. 9 is a side cross-sectional view of the visor, as assembled.

FIG. 10 is a rear perspective view of the visor, as assembled.

FIG. 11 is a top perspective view of the plastic headband.

FIG. 12 is a top perspective view of the visor, as assembled.

DESCRIPTION OF THE PREFERRED EMBODIMENT

A method for assembling the visor will first be described in the chronological order in which the steps will take place.

Figure 1:
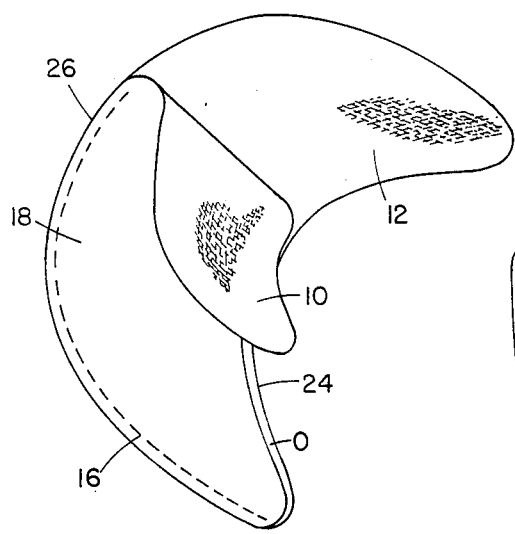
FIG. 1 is a top view of the pocket during the assembly.

As shown in FIG. 1 the first step comprises the joining of the fabric covering the top 10 and bottom 12 of the bill 28 (FIG. 12) of the visor 100. Two pieces of fabric are cut in a crescent shape, with the fabric to be used as the bottom 12 of the bill 28 being cut slightly larger than the fabric used as the top 10 of the bill 28. In the present embodiment, the overlap O of the bottom 12 will be approximately 3/16 of an inch, but the overlap O will only be necessary along the inner edge 24 of the fabric. The fabric used is a 65/35 cotton-polyester blend fabric, although any fabric well known in the art can be used. After cutting the top 10 and bottom 12, it if is desired to crimp, stitch or affix any label or slogan 14 (shown in FIG. 2) to the fabric to be used on the top 10 of the bill 28, this should be done next. As shown in FIG. 1, the top 10 and bottom 12 are then aligned, with the surface of the top 10 and bottom 12 which will form the exterior of the bill 28 facing each other. The top 10 and bottom 12 are then sewn together at a first seam 16 along the outer edge 26 of the crescent to form a pocket 18. The inner edge 24 of the pocket 18 is not sewn together at this time. The present embodiment employs a Singer 240W3 sewing machine to perform this task with eight stitches per inch, although this is subject to any variations in stitching or sewing machines well known in the art.

Figure 2:
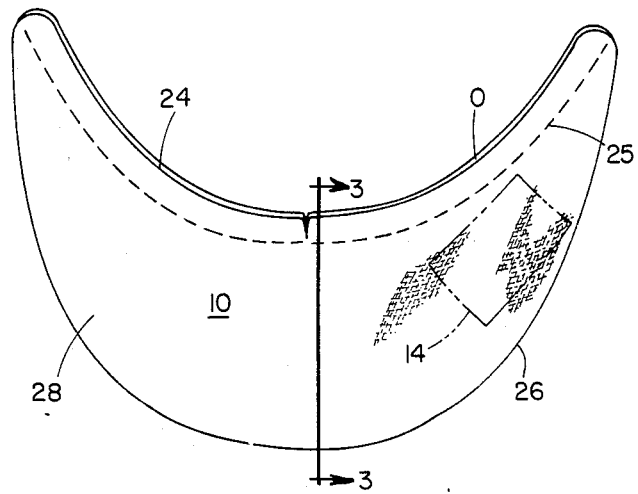
FIG. 2 is a top view of the bill as assembled.
Figure 4:
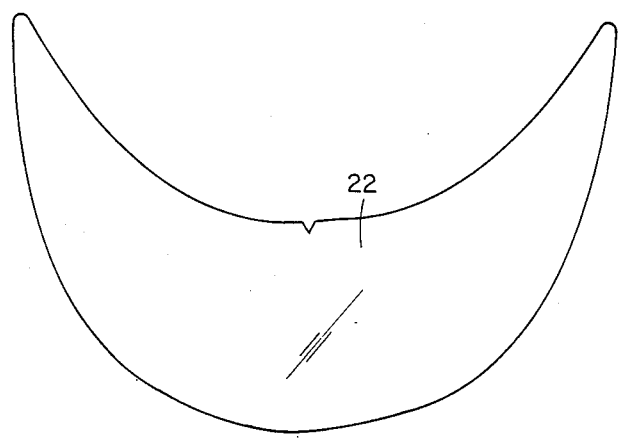
FIG. 4 is a top view of the plastic bill insert.
Figure 3:
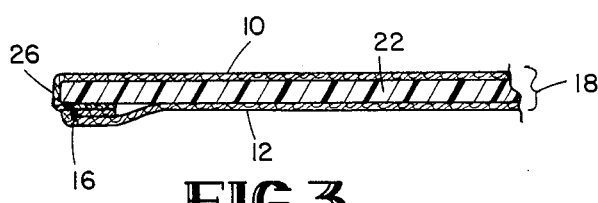
FIG. 3 is a cross-sectional view of the bill taken along the lines 33 of FIG. 2.

The next step requires that the pocket 18 be inverted in order to conceal the first seam 16 along the inside of the pocket 18 as shown in FIG. 2 and 3. Then, a crescent shaped sheet of plastic 22, shown in FIG. 4, is inserted into the pocket 18 to form the bill 28, as shown in FIGS. 2 and 3. The plastic 22, shown in FIG. 4, is of a type well known in the art, and is flexible, but with enough rigidity to hold a form in the bill 28. The plastic 22 is cut in dimensions almost identical to the top 10, except that it is slightly smaller to allow for the reduction in surface area of the top 10 due to the inversion of the pocket 18 (FIG. 2) and to allow for the plastic 22 to be recessed slightly in the pocket 18. The plastic 22 is initially flat, so that when inserted into the pocket 18, it forms a relatively flat pocket 18. The pocket 18 is then stitched together to complete the bill 28 as shown in FIG. 2. The stitching may be done near the outer edge 26 of the pocket 18 or the inner edge 24. The decision as to which edge to stitch will be affected by the size of the label 14. If the label 14 is large, the stitching may be along the inner 24 edge to avoid stitching through the lable 14. In either case, the stitching will be approximately ½ inch from the respective edge, with the ½ inch being measured from the overlapping bottom 12 if the stitching is along the inner edge 24. If the stitching is along the inner edge 24, the plastic 22 should be recessed in the pocket 18 just enough so that the stitching merely closes the pocket 18 and does not engage the plastic 22. This stitching is also contemplated as being performed by a Singer 240W3 sewing machine, with 8 stitches per inch. After the stitching is completed, the bill 28 of the visor has been formed. FIGS. 2, 6, 7, 8, 9, 10 and 12 show a bill 28 which has been stitched along the inner edge 24. This stitching is labeled the second seam 25, as shown in FIG. 2.

After stitching the second seam 25 to form the bill 28, the bottom 12 of the bill 28 will still overlap O the top 10 along the inner edge 24. This inner edge 24 may be trimmed to remove loose threads. The present embodiment accomplishes the task with a Singer 245-4 cutter.

Figure 5:
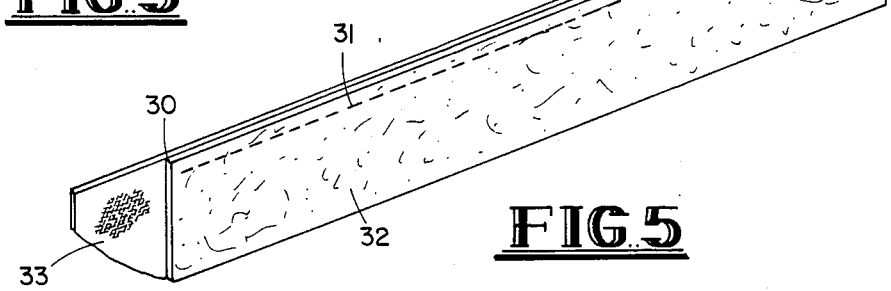
FIG. 5 is a side perspective view of the front piece, as assembled.

The end result of the next step in the assembly process is shown in FIG. 5. As partially shown in this figure, a strip of cloth 30 approximately 18 inches long and 1¾ inches wide is stitched along one edge at a third seam 31, lengthwise, to a piece of wadding 32 approximately 16 inches long and approximately the same width as the cloth 30. The joining of the cloth 30 and wadding 32 along the third seam 31 forms a front piece 34. The wadding 32 is a resilient, sponge-like layer of material used in the present embodiment for further cushioning the headband. The material used presently is 900 HF Pellon, manufactured by Texas Speciality Co., although any other material well known in the art may be used. The cloth 30 should match the cloth used as the top 10 of the bill 28. Other lengths and widths of cloth 30 or wadding 32 may be used as appropriate for different head sizes.

The next act in assembling the visor 100 (FIG. 10) is shown in FIG. 6. The front piece 34 is centered along the top 10 of the bill 28. The front piece 34 is longer than the inner edge 24 and should overlap. The third seam 31 of the front piece 34 is aligned, cloth 30 side down, along the second seam 25, assuming the second seam 25 has been stitched along the inner edge 24. The third seam 31 faces the inner edge 24 of the bill 28 and the unstitched edge of the front piece 34 faces towards the outer edge 26. The machine used to attach the front piece 34 to the bill 28 in the present embodiment is a Singer 153W102 sewing machine, sewing approximately six stitches per inch. The machine contains what is known as a "cylinder arm", which is a round cylindrical protrusion which acts as the stitching surface of the machine. The front piece 34 is centered on the bill 28 with the top 10 facing up from the cylinder arm. One end 36 (not shown) of the inner edge 24 of the bill 28 is introduced onto the cylinder arm along with the now aligned front piece 34. The front piece 34 and the bill 28 are then stitched together and the cylinder arm turns the front piece 34 to follow the curvature of the inner edge 24 of the bill 28. The front piece 34 and bill 28 are stitched together almost along the same line as the third seam 31 and the second seam 25, if such second seam 25 exists. This fourth seam, labeled 38, will also not engage the plastic 22.

The next step in the assembly process, shown in FIG. 7, involves attaching a sweat band 40 to the visor 100. A sweat band 40 is used in the present embodiment to absorb sweat and to cushion the material used as the backbone of the partial headband, to be explained later. The sweat band 40 is shown in more detail in FIG. 8 and is comprised of a cloth covering 42, a foam strip 44 and plastic film 46. The sweat bands 40 can be purchased already assembled from some manufacturers, and Applicant purchases such sweat bands 40 from Western Textiles. The assembled sweat bands 40 are manufactured in continuous rolls, so that a person assembling the visor 100 need merely unroll the desired length of sweat band 40 and cut the section off. The sweat bands 40 used in the present embodiment are approximately 1 and ¼ inches wide and ⅛ inch thick. Of course, variations in size and materials can be used to accommodate different size visors. The sweat bands 40 are assembled by laying a strip of foam 44 and plastic film 46 along the center of a relatively wider strip of cloth 42. The strip of cloth 42 is then folded over the foam 44 and plastic film 46 and stitched along a pair of fifth seams 50 along each edge 48.

Refering back to FIG. 7, the sweat band 40 is centered along the bottom 12 of the bill 28, with the side of the sweat band 40 containing the plastic film 46 facing toward the bottom 12. Sweat band 40 is placed so that only one edge 48 will be in contact with the inner edge 24 of the bill 28, and the rest of the sweat band 40 will lap over the inner edge 24. The front piece 34 is folded away from the inner edge 24, because it has a natural inclination to stand up due to the curvature of the inner edge 24. The sweat band 40 will be at a length approximately equal to that of the wadding 32. Again, a cylinder arm type sewing machine such as the Singer 153W102 is used in the present stage of the assembly. The sweat band 40 fifth seam 50 is aligned with the third seam 31 and four the seam 38. The front piece 34 and sweat band 40 are stitched together on the cylinder arm starting at the wadding 32 and continuing along third seam 31. Beginning at bill 28, this sixth seam 52 joins fourth and second seams 38 and 25, and continues on to the other end of the wadding 32. FIG. 7 only shows the sixth seam 52 as being partially completed. If it is desired to attach any manufacturers labels to the inside of the sweat band 40, they may be attached during the stitching of the sixth seam 52 by stitching them onto the sweat band 40.

Referring to FIG. 7a, after the sixth seam 52 is completed (not shown) to the end of the sweat band 40, the front piece 34 will be folded back towards the inner edge 24 and aligned with the sweat band 40. The cloth 30 of the front piece 34 will overlap both the wadding 32 and the sweat band 40 at their respective ends 33. The ends 33 of the cloth 30 will be tucked inside of the sweat band 40 as shown in FIG. 7a. Using a cylinder arm type sewing machine, the front piece 34 and sweat band 40 will be stitched together along seventh seam 54, as shown in FIG. 7a. If a manufacturer's label is being attached, this will be incorporated into the sweat band 40 by securing it along the seventh seam 54.

Because the stitching together of the front piece 34 and sweat band 40 by seventh seam 54 leaves an exposed seam on the visor 100, an overlap piece 58, shown in FIG. 9 and 10, is added to seal the seventh seam 54. The overlap piece 58 is comprised of a strip of cloth approximately one and one-quarter inches wide and twenty inches long in the present embodiment. As shown in FIG. 9, the overlap piece 58 is folded towards the center of the strip of cloth and introduced into the cylinder arm to begin the stitching. The visor 100 is then introduced into the cylinder arm along the seventh seam 54 and an eighth seam 60 stitches the overlap piece 58 on top of the seventh seam 54 to the visor 100.

As evident from FIGS. 10 and 12, small excess pieces of the overlap piece 58 should be left at both ends of the now-assembled head piece 62. One end of the overlap piece 58 should be tucked into the tunnel formed in the head piece 62 by the seventh seam 54 (FIG. 9) and this end of the head piece 62 should be sewn closed along the ninth seam 64 as shown in FIG. 10. A semi-rigid plastic headband 66, shown in FIG. 11, is inserted into the head piece 62 at the open end of the head piece 62. The present embodiment uses a plastic manufactured by Textek Plastics, Inc., which is approximately ⅛ inch wide, ⅝ inches high, and 15 inches long for the headband 66. The semi-rigid plastic headband 66 forms the backbone of the head piece 62 and is formed in a semi-circular shape contoured to fit around a person's head. After the headband 66 is inserted into the open end of the head piece 62, it should fit completely inside the head piece 62. Finally, the overlap piece 58 at the open end of the head piece 62 is tucked into the head piece 62 and closed by a seam identical to the ninth seam 64, as shown in FIG. 10.

Finally, if desired, the visor may be steamed and blocked to remove wrinkles.

The finished product is shown in FIGS. 10 and 12. The visor 100 is attractive and very durable because of the high quality of materials used and the fact that all cloth edges will be hidden from the exterior of the visor 100 where they might fray or unravel. Different perspective views of the visor 100 as finished, are shown in FIGS. 10 and 12, with a cross-sectional view shown in FIG. 9. The head piece 62, supported by the headband 66 forms a semi-rigid and semi-circular head piece 62 for gripping the head of a person. The cloth covering 42 and the foam strip 44 of the sweat band 40 will cushion the head from the headband 66 to provide a comfortable fit for the visor 100. By varying the length and shape of the headband 66 and the parts covering the headband 66, the visor 100 can be manufactured for any size or shape of head. The headpiece 62 does not completely encircle the head.

Although the visor and assembly method have been described in the foregoing embodiment, the invention taught by this disclosure is capable of many variations that are within the scope of the present invention. In particular, but not by way of limitation, other materials may be used which would change the invention or make it unnecessary to conceal all seams, different forms of joining the various pieces can be used besides stitching, the order of assembly could be changed, and any other variations could be made which would be obvious to one skilled in the art.

We claim:

1. A method of assembling a visor which does not compltely encircle the head of the person wearing the visor comprising:
   joining crescent-shaped pieces of fabric to form a pocket;
   inserting a crescent-shaped sheet of plastic into the pocket to form a bill;
   stitching an elongated strip of wadding to an elongated strip of cloth along a first edge thereof to form a front piece;
   stitching the front piece to the bill along a seam along the first edge of the elongate strip of cloth;
   stitching a first edge of an elongate sweat band to the front piece along the first edge of the elongate strip of cloth;
   stitching a second edge of the sweat band to a second edge of the elongate strip of cloth;
   stitching an overlap piece to the front piece and the sweat band along the second edge thereof;
   inserting a semi-rigid headband into the sweat band; and
   stitching the ends of the overlap piece and the front piece closed.

2. The method of claim 1 additionally comprising inverting the pocket before inserting the crescent-shaped piece of plastic therein.

3. The method of claim 1 additionally comprising stitching the pocket closed after the crescent-shaped piece of plastic is inserted.

4. The method of claim 3 wherein the front piece is stitched to the bill along the seam closing the pocket.

5. The method of claim 1 additionally comprising folding the front piece over the elongate sweat band before stitching the second edge of the sweat band to the second edge of the elongate strip of cloth.

6. A visor which does not completely encircle the head of the person wearing the visor comprising:
   a crescent-shaped sheet of plastic;
   a top and a bottom piece of fabric sewn together by a first seam to form a pocket containing said crescent-shaped sheet of plastic therein, said pocket being closed by a second seam to form a bill;
   an elongate strip of cloth;
   an elongate strip of wadding, said strip of wadding being stitched to said strip of cloth by a third seam to form a front piece, said front piece being joined to said bill by a fourth seam along said second and third seam; and
   an elongate sweat band having a fifth seam along the edges thereof, said sweat band being joined to said front piece by a sixth seam along said second, third, and fourth seams.

7. The visor of claim 6 wherein said sixth seam joins one edge of said sweat band to said front piece and a seventh seam joins the other edge of said sweat band to said front piece.

8. The visor of claim 7 wherein said seventh seam joins the other edge of said sweat band to the elongate strip of cloth and the wadding of said front piece.

9. The visor of claim 7 additionally comprising an overlap piece stitched by an eighth seam to said front piece.

10. The visor of claim 9 wherein said eighth seam is stitched along said seventh seam.

11. The visor of claim 6 additionally comprising a semirigid headband inside said front piece.

12. The visor of claim 6 wherein said sweat band comprises a foam strip enclosed within a strip of plastic film and a cloth covering the plastic film and the cloth covering being joined by said fifth seam.

* * * * *